United States Patent [19]

Tykulsky et al.

[11] Patent Number: 4,640,292
[45] Date of Patent: Feb. 3, 1987

[54] EXTENDING SAMPLE VOLUME IN PULSED DOPPLER SYSTEMS

[75] Inventors: Alexander Tykulsky, Carlisle; Karl E. Thiele, Melrose; Leslie I. Halberg, Malden, all of Mass.

[73] Assignee: Hewlett-Packard Company, Palo Alto, Calif.

[21] Appl. No.: 827,670

[22] Filed: Feb. 10, 1986

Related U.S. Application Data

[63] Continuation of Ser. No. 619,881, Aug. 24, 1984, abandoned.

[51] Int. Cl.$^4$ ............................................. A61B 10/00
[52] U.S. Cl. .................................. 128/661; 128/663; 73/861.25; 367/90
[58] Field of Search .............................. 128/661, 663; 73/861.25; 367/90

[56] References Cited

U.S. PATENT DOCUMENTS

| | | | |
|---|---|---|---|
| 4,067,236 | 1/1978 | Hottinger | 73/861.25 |
| 4,103,679 | 8/1978 | Aronson | 128/663 |
| 4,104,912 | 8/1978 | Clavelloux et al. | 367/90 |
| 4,217,909 | 8/1980 | Papadofrangakis et al. | 128/663 |
| 4,413,630 | 11/1983 | Anderson et al. | 128/661 |
| 4,476,874 | 10/1984 | Taenzer et al. | 128/663 |

FOREIGN PATENT DOCUMENTS 0133040 11/1978 Fed. Rep. of Germany ...... 128/663

OTHER PUBLICATIONS

Peronneau et al., "Real-Time Measurement of Blood Velocity Profiles by Ultrasonic Multigated Pulsed Doppler Velocimeter", the Third International Conference on Medical Physics, 1972.

Brandestini, "Topoflow-A Digital Full Range Doppler Velocity Meter", IEEE Transactions on Sonics and Ultrasonics, vol. SU-25, No. 5, Sep. 1978, pp. 287-293.

Primary Examiner—Kyle L. Howell
Assistant Examiner—Ruth S. Smith
Attorney, Agent, or Firm—Donald N. Timbie

[57] ABSTRACT

The sampling volume of a pulsed Doppler system is increased to a length greater than that corresponding to one pulse by sampling the reflections of each launched pulse a plurality of successive times and accumulating the samples.

4 Claims, 8 Drawing Figures

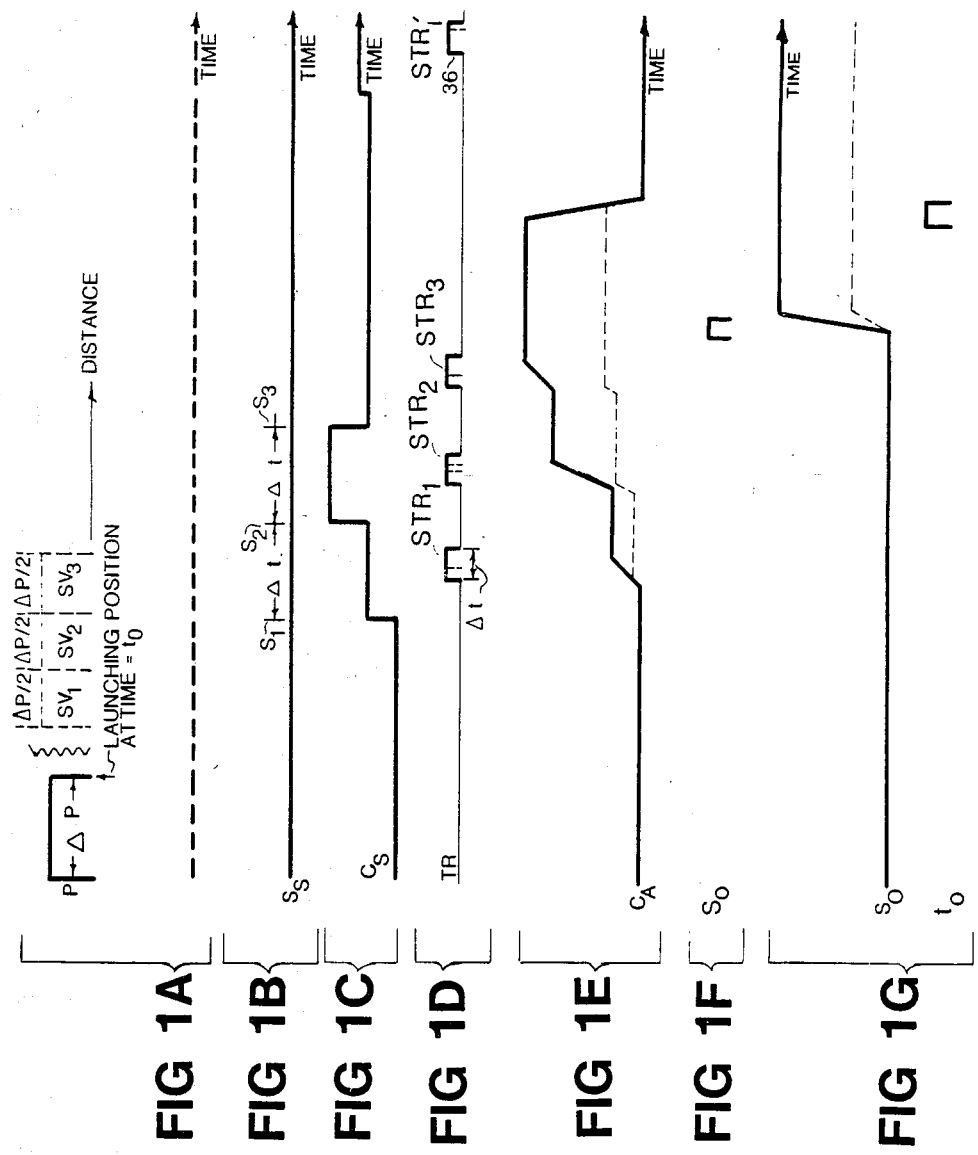

EXTENDING SAMPLE VOLUME IN PULSED DOPPLER SYSTEMS

CROSS REFERENCE TO RELATED APPLICATION

This application is a continuation of application Ser. No. 619,881, filed Aug. 24, 1984, now abandoned.

BACKGROUND OF THE INVENTION

Doppler stated that waves reflected by an object have the same frequency as the waves incident thereon if the distance between the object and the source of the waves is constant, a higher frequency if the distance is decreasing, and a lower frequency if the distance is increasing. It is therefore possible to determine the velocity of an object with respect to the source by noting the difference between the frequencies of the waves emanating from the source and the waves reflected from the object.

This principle has been used to determine the respective velocities of a large number of particles, known in the art as "scatterers", that are moving in a stream flowing in a non-homogeneous medium, e.g., the respective velocities of particles of blood flowing in an artery, vein or heart chamber of a patient. In the usual apparatus for performing this function, pulses of pressure waves of a known frequency are launched by a transducer at a constant repetition rate into the medium along a path intersecting the stream. Energy contained in these pulses is reflected back to the transducer from locations along the path at which there is a change in acoustical impedance. Particles contained in blood generally constitute such variations in impedance. The transducer converts the reflected pressure waves into electrical waves, and means are provided for sampling the electrical waves at a time after the launching of said pulse at which the electrical waves relate to pressure waves reflected from scatterers of interest. Because the scatterers are moving, the amplitude of successive samples will change. Fourier analysis of this set of samples yields the respective amplitudes of a plurality of discrete frequencies. Each frequency corresponds to a different velocity, and its amplitude corresponds to the number of scatterers moving at that velocity. It is also possible to obtain an impression of the velocities of the scatterers by listening to a loudspeaker that is connected to the source of the samples with a suitable filter.

For reasons which are understood by those skilled in the art, the amplitude of each sample is proportional to the summation of reflections from scatterers contained in a sample volume having a length along the path equal to one-half of the product of the velocity of propagation of the wave and the duration of the pulse. Unfortunately, however, there are many situations where the length of the sample volume is not great enough to extend across the stream of scatterers for which the velocities are being sought, e.g., when the stream is flowing through one of the ventricles of a heart. This means that no indication will be attained of the velocities of scatterers along the path that do not lie within the sample volume. In order to include these scatterers in the sample volume, it has been customary to increase the duration of the pulses. However, where there is a limit to the power of the pulses that may be used as, for example, when pulses of pressure waves are being introduced into a patient's body for the purpose of measuring blood velocity, it is necessary to reduce the amplitude of the pulses when their duration is increased. It is also necessary to alter the receiver for each change in duration of the pulses if the signals are to be processed efficiently. The equipment required for these purposes is complex and expensive.

BRIEF SUMMARY OF THE INVENTION

In accordance with this invention, the sample volume is effectively increased by taking additional samples of the reflections of each launched pulse and accumulating the samples. The usual first sample is taken at such time that its sample volume extends from the near side of the stream of scatterers, and a required number of additional samples are taken at successively later instants of time so that their respective sample volumes combine to effectively straddle the stream. If the time between samples is equal to the duration of a pulse, the end of one sample volume will abut the beginning of the next, but the time between samples could be shortened so that the adjacent ends of the sample volumes overlap, or the time between samples could be increased so that there are gaps between the sample volumes. The sum of the samples can be made to have the same information as a sample taken from the reflection of a launched pulse that is lengthened so as to cross the stream in accordance with the prior art.

One apparatus for carrying out the method described above employs an input sampler for providing a voltage equal to the amplitude of each sample and an accumulator for summing or averaging the voltages. The accumulator is cleared after the sum for all the samples associated with each launched pulse is obtained. The output of the accumulator can be applied to means for performing a Fourier analysis, such as an FFT, but if this is done, filters must be employed to attenuate the sampling transients resulting from the addition of each sample voltage and the clearing before accumulation. In accordance with another aspect of this invention, filters for attenuating these sampling transsients can be simplified by coupling an output sampler of the sample-and-hold type to the output of the accumulator and causing it to sample after the accumulator attains its final sum. Samples of the output of the output sampler are then applied to an FFT.

BRIEF DESCRIPTION OF THE DRAWINGS

FIG. 1A illustrates a launched pulse and some sample volumes;

FIG. 1B illustrates a plurality of samples;

FIG. 1C illustrates the voltage built up on an input capacitor;

FIG. 1D illustrates the timing of a switch that transfers the voltage on the input capacitor to the accumulator;

FIG. 1E illustrates the build-up of voltage by the accumulator;

FIG. 1F illustrates the timing of a sample-and-hold circuit that is coupled to the output of the accumulator;

FIG. 1G illustrates the output of the sample-and-hold circuit; and

FIG. 1H illustrates the timing of a switch that clears the accumulator.

DETAILED DESCRIPTION OF THE INVENTION

Figure 1:
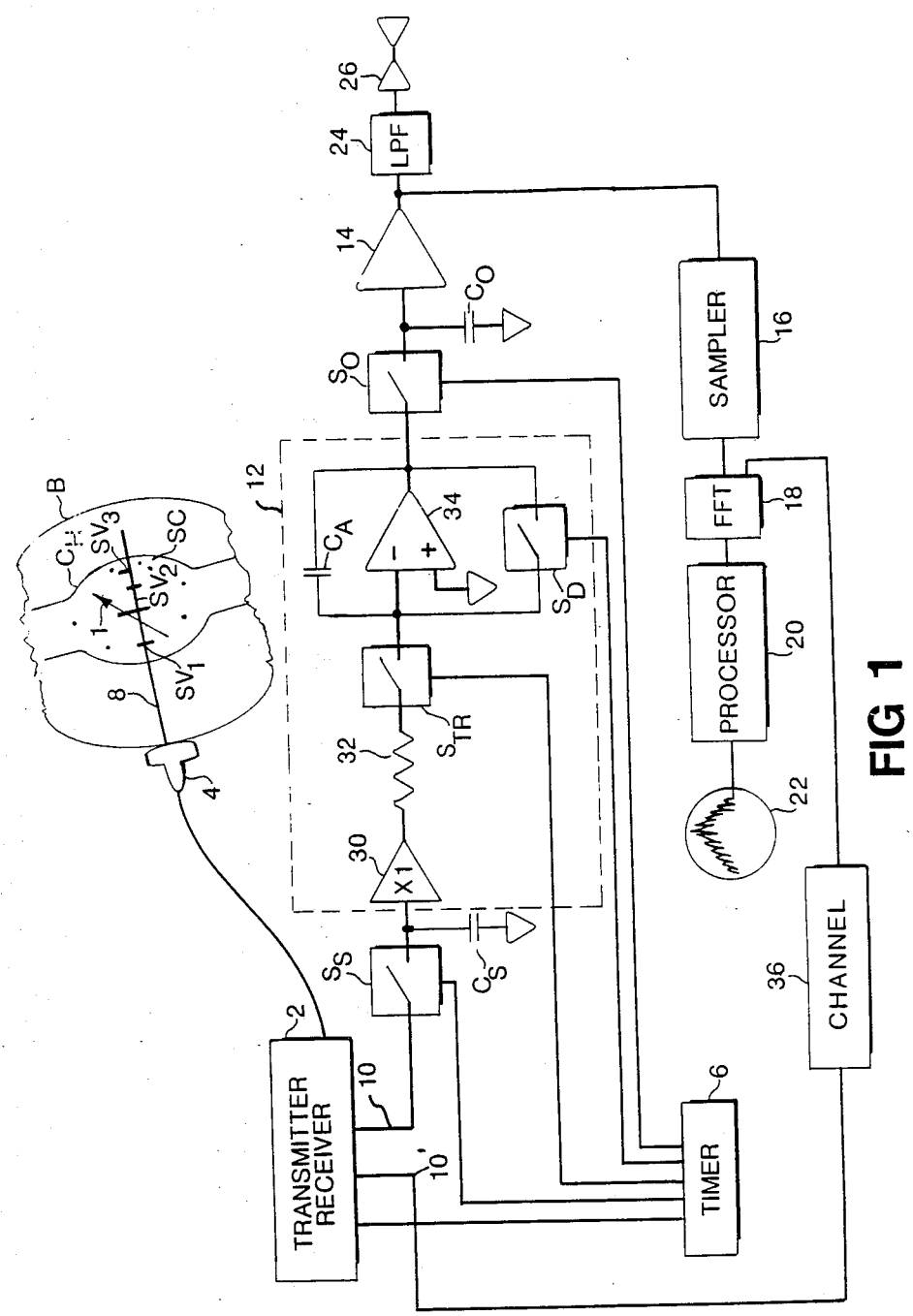
FIG. 1 is a schematic diagram of one form of apparatus for carrying out the invention.

Reference is now made to FIG. 1. The invention will now be described as it would be used to measure the velocities of blood particles flowing in the general direction of an arrow 1 through a heart chamber CH contained within the body B of a patient. The relative size of the chamber CH is exaggerated for explanatory purposes. A transmitter/receiver 2 causes a transducer 4 that is in intimate physical contact with the body B to launch pulses of several cycles of pressure variation at a given repetition rate controlled by a timer 6 along a path 8 so as to intersect the flow of blood indicated by the arrow 1. Reflections of some of the energy in the pressure waves of the launched pulses by blood particles indicated by dots SC travel back to the transducer 4 along the path 8 and are converted therein to corresponding voltage variations. These voltage variations or signals are amplified in the transmitter/receiver 2 and appear at its output 10.

The signals at the output 10 of the transmitter/receiver 2 are applied to a sampling means herein shown as being comprised of a sampling switch $S_S$ and a sample capacitor $C_S$ connected in the order named between the output 10 and ground. The switch $S_S$ is controlled by the timer 6. The junction of the switch $S_S$ and the capacitor $C_S$ is connected to the input of an accumulator 12 which is herein shown as being a current integrator, and the output of the accumulator 12 is connected, if desired, to an accumulator output sampling means herein shown as being comprised of an output switch $S_O$, that is controlled by the timer 6, and an output capacitor $C_O$ that are connected in series in the order named between the output of the accumulator 12 and ground. An amplifier 14 is connected between the ungrounded side of the capacitor $C_O$ and a sampler 16 for an FFT analyzer 18, and a processor 20 is coupled to the output of the FFT analyzer 18 so as to prepare the signals received therefrom for display on a display means 22. If desired, the sampled signals can be listened to by connecting a low pass filter 24, an audio amplifier 26, and a loudspeaker 28 to the output of the amplifier 14.

Although a different type of accumulator could be used for storing successive samples provided by the sampling means $S_S$, $C_S$, the accumulator 12 is comprised of a buffer amplifier 30 having its input connected to the ungrounded side of the sampling capacitor $C_S$. A series circuit comprised of a resistor 32 and a transfer switch $S_{TR}$ that may be connected in either order is connected between the output of the buffer amplifier 30 and the inverting input of an operational amplifier 34. The non-inverting input is connected to ground. An accumulating capacitor $C_A$ and a discharge switch $S_D$ are respectively connected between the output of the amplifier 34 and its inverting input. The switches $S_{TR}$ and $S_D$ are controlled by the timer 6.

The accumulator 12 operates as follows. The buffer amplifier 30 and the resistor 32 form a constant current source that provides current with an amplitude corresponding to the voltage across the sampling capacitor $C_S$. After each closure of the sampling switch $S_S$, the transfer switch $S_{TR}$ is closed so as to permit current corresponding to the voltage across the sampling capacitor $C_S$ to flow into the accumulating capacitor $C_A$ and increase the charge thereon. It is this net charge that is related to the summation of successive sample voltages appearing on $C_S$. And, of course, the voltage at the output of the operational amplifier 34 will follow the changes in voltage across $C_A$.

If the sampling switch $S_S$ is closed only once after the launching of each pulse, as would be the case if the sample volume were long enough, the transfer function of the accumulator 12, which is equal to $\Delta t/RC$ where $\Delta t$ is the time the transfer switch $S_{TR}$ is closed, R is the ohmic value of the resistor 32 and C is the capacitance of $C_A$, could be set at such a value that the maximum voltage expected at the output of the amplfiier 34 under normal operating conditions would be as large as possible without saturating subsequent circuits. But if, in accordance with this invention, the sampling switch $S_S$ is closed a plurality of times after each launched pulse so as to successively charge the sampling capacitor $C_S$ in accordance with the reflections from scatterers in the respective sample volumes $SV_1$, $SV_2$ and $SV_3$ of FIG. 1, and if the transfer function remains the same, the voltage at the output of the amplifier 34 could become large enough to saturate subsequent circuits. If, for example, $\Delta t/RC=1$, the accumulator 12 becomes a summing device that simply sums the successive sample voltages appearing across $C_S$ so that the voltage at the output of the amplifier 34 would be great enough to saturate subsequent circuits. This can be avoided by reducing the transfer function $\Delta t/RC$ in any of a number of ways. One way is to couple the transfer switch $S_{TR}$ to the timer 6 in such manner as to reduce the time $\Delta t$ during which it is closed. Other ways will readily occur to one skilled in the art such as, e.g., changing the value of the resistor 32 and/or the value of the capacitor $C_A$. In any case, if the transfer function is made equal to 1/n where n equals the number of samples, the voltage at the output of the amplifier 34 would be an average of the samples and would not exceed the voltage of a single sample. Instead of changing the transfer function as described, means could be provided for changing the voltage to which the sampling capacitor $C_S$ is charged, e.g., by connecting different valued resistors in series with it and controlling the time during which the sampling switch $S_S$ is closed.

After all of the samples following each launched pulse have been processed as described, the timer 6 closes the switch $S_D$ so as to discharge the accumulating capacitor $C_A$ in preparation for a new series of samples.

Although the voltage appearing at the output of the accumulator 12 could be used directly, the removal of the sampling transients caused by the charge and discharge of $C_A$ is simplified by using the output sample-and-hold device $S_O,C_O$ that is connected between the output of the accumulator 12 and the amplifier 14. The switch $S_O$ is closed for an instant by the timer 6 after the accumulator 12 has performed its last summing operation so that the capacitor $C_O$ is charged to the voltage at the output of the accumulator 12 occurring at this time. The voltage across the capacitor $C_O$ remains until $S_O$ is closed again and is coupled via the amplifier 14 to a sampler 16 that provides the samples that can be analyzed by a Fast Fourier Transform 18 so as to supply signals representing the amplitudes of discrete frequencies. A processor 20 is coupled to the output of the FFT 18 so as to derive signals representing the velocities of the various blood particles SC in such manner that they can be displayed on a cathode ray tube 22.

In the interest of simplification, only a single channel has been shown, but in order to determine the direction in which scatterers are flowing, a channel 36 similar to that just described is provided that is supplied with the signals at an output 10' of the transmitter/receiver 2 that are in phase quadrature with the signals at the output 10.

OPERATION

Reference is now made to FIGS. 1A through 1H for an explanation of the operation of FIG. 1. In FIG. 1A, the leading edge of a pulse P that is about to be launched is shown as occurring at $t_0$. Inasmuch as the pulse P travels at a uniform velocity, FIG. 1A is a spacial plot of the position of the pulse at different times. The length of P is $\Delta P$. The timer 6 supplies a series of pulses that are $\Delta t$ seconds apart to the sampling switch $S_S$ when the received reflections are from the scatterers at the range of interest. The successive samples $S_1$, $S_2$ and $S_3$ thus derived are shown in FIG. 1B as respectively having three units, six units and three units of amplitude. As shown in FIG. 1C, the voltage across $C_S$ quickly assumes and holds the value of each sample. After each of the samples $S_1$, $S_2$ and $S_3$ are taken, the timer 6 closes the transfer switch $S_{TR}$ for a period of time $\Delta t$ as shown at $S_{TR1}$, $S_{TR2}$ and $S_{TR3}$ in FIG. 1D. During each closure of the switch $S_{TR}$, the capacitor $C_A$ is charged by current from the constant current source 30, 32. The current has a value proportional to the voltage across $C_S$. If the transfer function $\Delta t/RC$ is unity, the successive samples will be summed at the output of the amplifier 34, as indicated by the solid line in FIG. 1E; but if the transfer function is reduced to one-third by closing $S_{TR}$ for a shorter period $\Delta t/3$, the maximum output of the amplifier 34 and therefore of the accumulator 12 will be the average of the samples, or four units, as indicated by the dashed line in FIG. 1E.

If the output sampler $S_O, C_O$ is not used, the output of the accumulator 12 is applied to the input of the sampler 16 via a filter, not shown; but if the output sampler $S_O, C_O$ is used, its switch $S_O$ is closed by the timer 6 after all the samples have been applied to the accumulator 12 as indicated in FIG. 1F. This quickly charges the capacitor $C_O$ to the voltage at the output of the accumulator 12. As indicated in FIG. 1G, this would be twelve units if $S_{TR}$ were closed for $\Delta t$ seconds as indicated by the solid line, and four units if $S_{TR}$ were closed for $\Delta t/3$ as indicated by the dashed line. After the sampler 16 has taken a sample, the timer 6 closes the switch $S_D$ for a brief interval as indicated in FIG. 1H so as to discharge $C_A$ as shown in FIG. 1E before the next set of samples is received.

When the samples $S_1$, $S_2$ and $S_3$ are taken, the respective sample volumes $SV_1$, $SV_2$ and $SV_3$ are located as indicated in FIG. 1A.

What is claimed is:

1. A method for operating an ultrasonic pulsed Doppler system in such manner as to obtain the velocity distribution of scatterers along the path of the Doppler pulse and within a volume having a length along the line of propagation of the pulse that is greater than the length of the sample volume, defined by the length of said Doppler pulse, along the line of propagation, comprising the steps of:
   launching pulses of alternating waves at a given rate into a medium containing the scatterers,
   obtaining a plurality of samples of the reflections of each launched pulse at respectively successive times so that each sample is of the reflections of scatterers contained in a different sample volume,
   accumulating said samples so as to derive an accumulated sample to which all samples contribute, and
   coupling the accumulated sample to processing means therefor to provide a signal representative of Doppler shift encompassed by all said different sample volumes.

2. A method such as set forth in claim 1 in which the samples are weighted before they are accumulated.

3. In an ultrasonic pulsed Doppler system, apparatus for deriving the velocity distribution of scatterers along the path of the Doppler pulse and with a volume having a dimension along the path of propagation of the pulses that is greater than the corresponding dimension of the sample volume, defined by the length of said Doppler pulse, comprising
   means for launching pulses of alternating waves at a given rate into a medium containing scatterers,
   means for obtaining a plurality of samples of the reflections of each launched pulse at respectively successive times so that each sample is of the reflection of scatterers contained in a different sample volume,
   means for accumulating said samples so as to derive an accumulated sample to which all samples contribute, and
   means for processing the accumulated sample to provide a signal representative of Doppler shift encompassed by all said different sample volumes.

4. Apparatus as set forth in claim 3 wherein means are provided for weighting the samples before they are applied to the accumulating means.

* * * * *